(12) United States Patent
Ditzel et al.

(10) Patent No.: US 8,394,983 B2
(45) Date of Patent: *Mar. 12, 2013

(54) PROCESS FOR THE CARBONYLATION OF DIMETHYL ETHER

(75) Inventors: Evert Jan Ditzel, Goole (GB); David John Law, Beverley (GB); Mark Stephen Roberts, Beverley (GB)

(73) Assignee: BP Chemicals Limited, Middlesex (GB)

( * ) Notice: Subject to any disclaimer, the term of this patent is extended or adjusted under 35 U.S.C. 154(b) by 226 days.

This patent is subject to a terminal disclaimer.

(21) Appl. No.: 12/450,988

(22) PCT Filed: Apr. 23, 2008

(86) PCT No.: PCT/GB2008/001474
§ 371 (c)(1),
(2), (4) Date: Oct. 21, 2009

(87) PCT Pub. No.: WO2008/132468
PCT Pub. Date: Nov. 6, 2008

(65) Prior Publication Data
US 2010/0130771 A1    May 27, 2010

(30) Foreign Application Priority Data
Apr. 26, 2007 (EP) .................................. 07251758

(51) Int. Cl.
C07C 67/36 (2006.01)

(52) U.S. Cl. ........................................ 560/232; 560/129
(58) Field of Classification Search .................. None
See application file for complete search history.

(56) References Cited

U.S. PATENT DOCUMENTS

| 6,387,842 | B1 * | 5/2002 | Wegman et al. | 502/300 |
| 7,465,822 | B2 * | 12/2008 | Cheung et al. | 560/232 |
| 2006/0252959 | A1 * | 11/2006 | Cheung et al. | 560/232 |

FOREIGN PATENT DOCUMENTS

WO   WO 2006/121778   11/2006

OTHER PUBLICATIONS

International Search Report for PCT/GB2008/001474, mailed Aug. 20, 2008.
Written Opinion of the International Searching Authority for PCT/GB2008/001474, mailed Aug. 20, 2008.
Tartamella, T.L. et al, "Role of Acid Catalysis in Dimethyl Ether Conversion Processes", Proceedings-Annual International Pittsburgh Coal Conference, 13$^{th}$ (vol. 2), pp. 996-1001, (1996).

* cited by examiner

*Primary Examiner* — Sudhakar Katakam
(74) *Attorney, Agent, or Firm* — Nixon & Vanderhye

(57) ABSTRACT

Process for the production of methyl acetate by the carbonylation of a dimethyl ether feed with carbon monoxide under substantially anhydrous conditions, in the presence of a zeolite catalyst effective for the carbonylation. The carbonylation is carried out at a temperature in the range of greater than 250° C. to 350° C. and at a pressure in the range of greater than 10 barg to 100 barg.

12 Claims, 11 Drawing Sheets

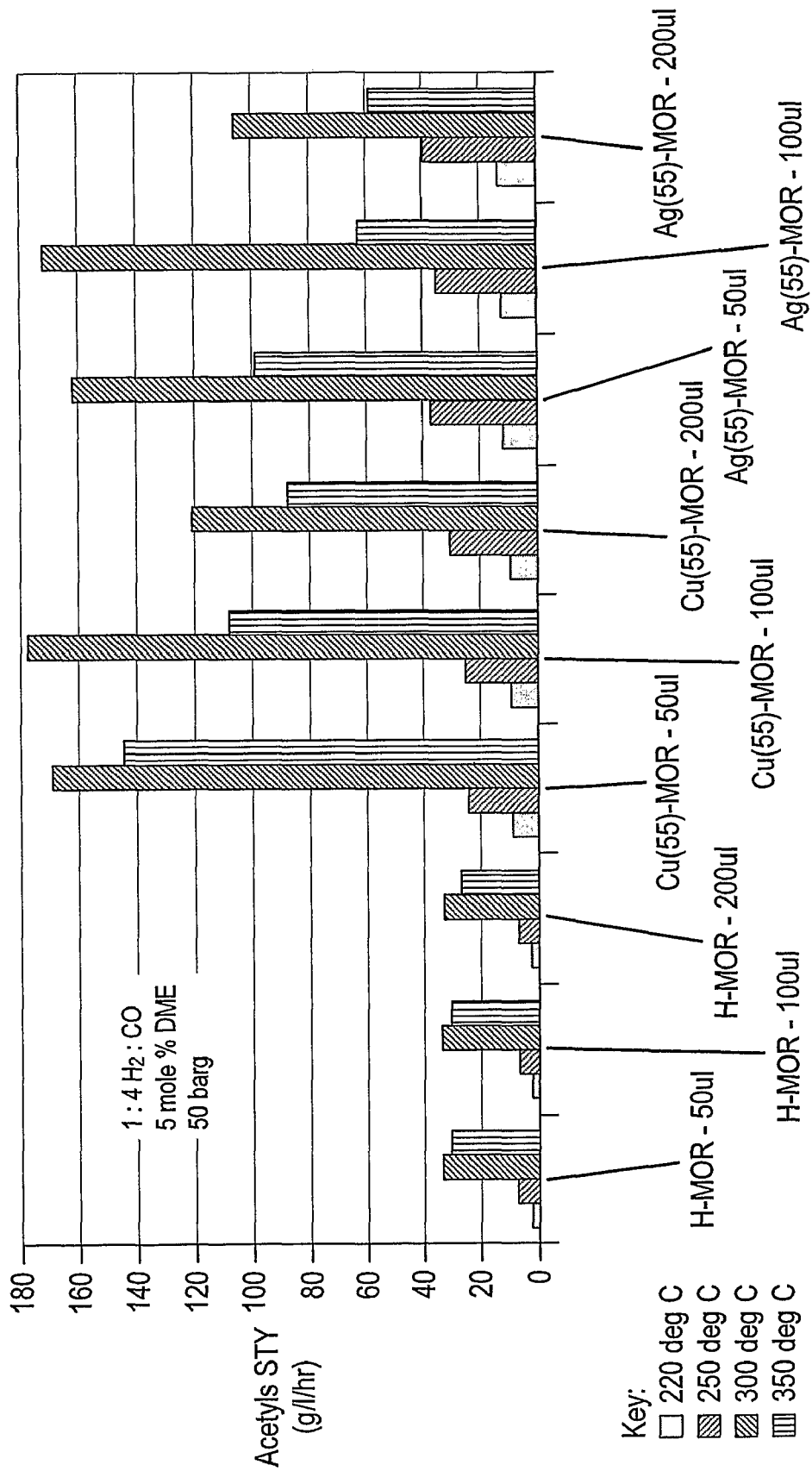

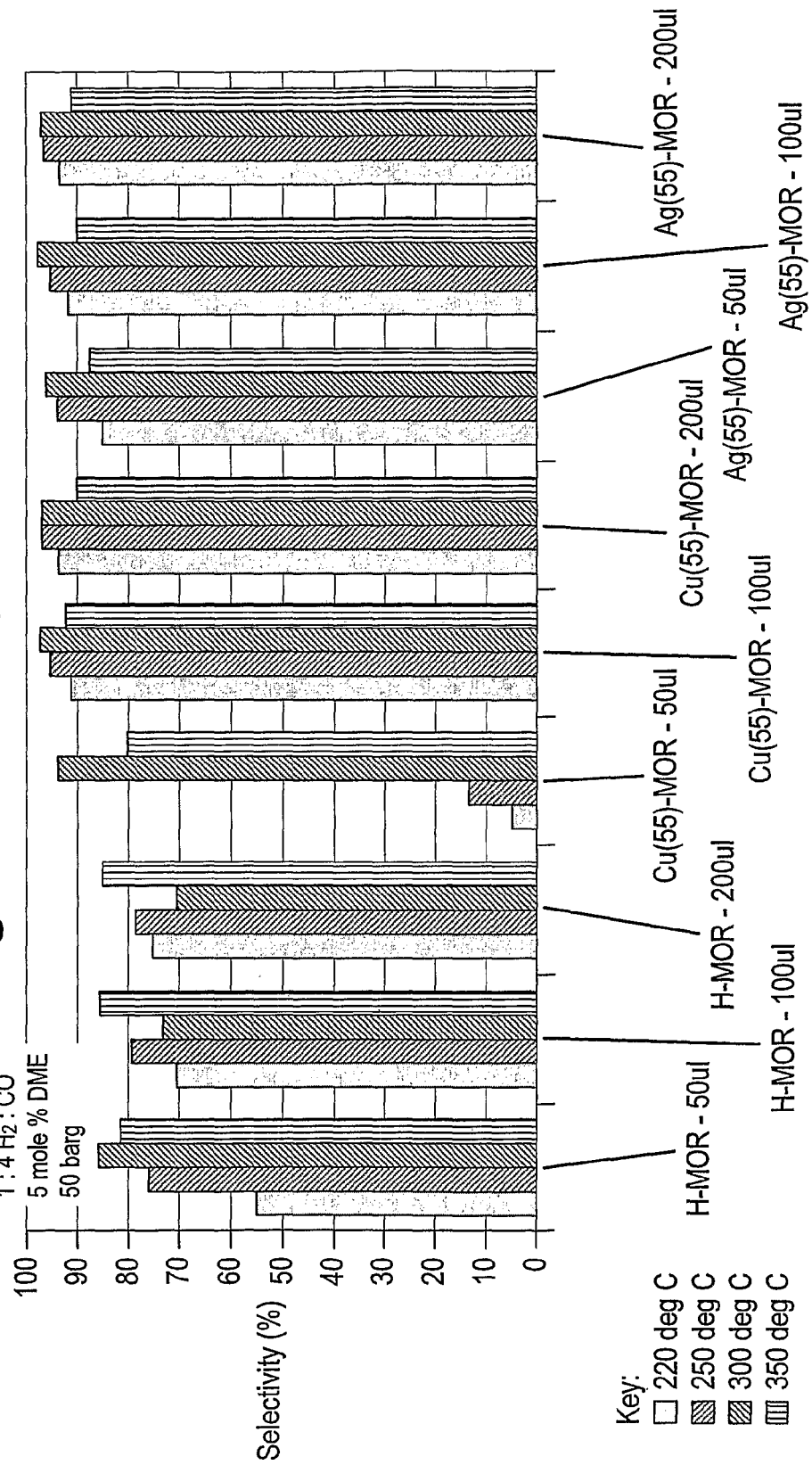

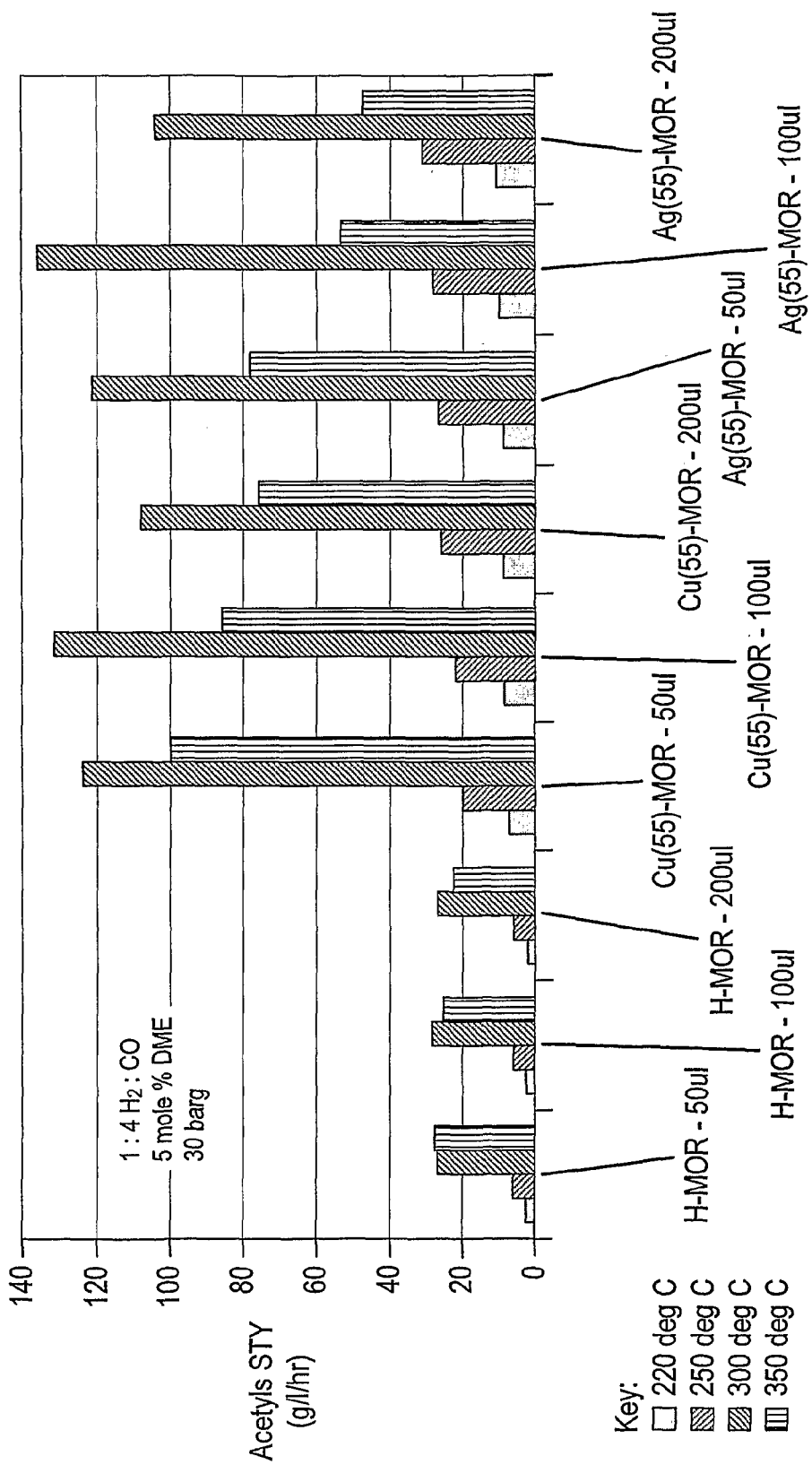

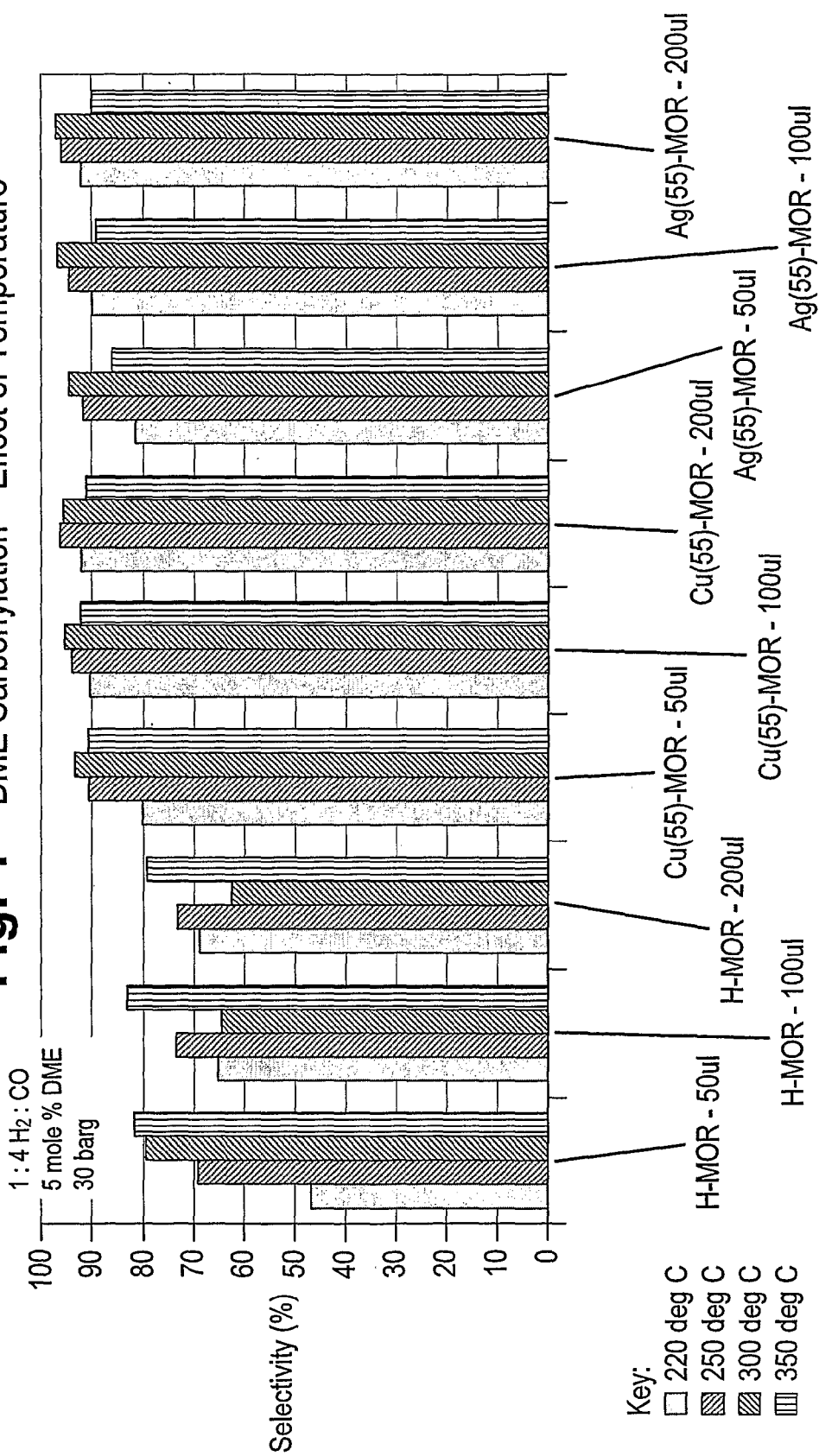

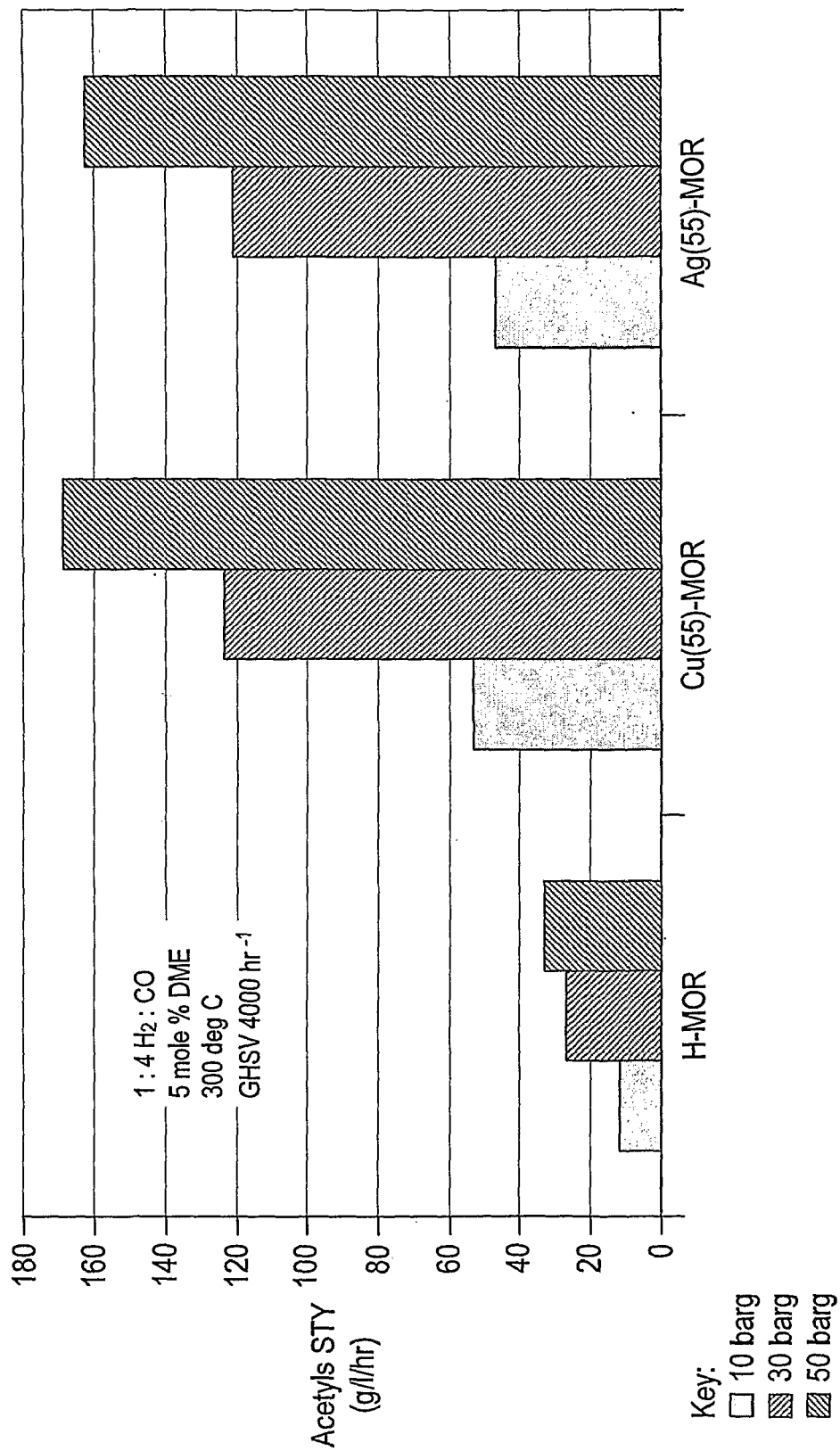

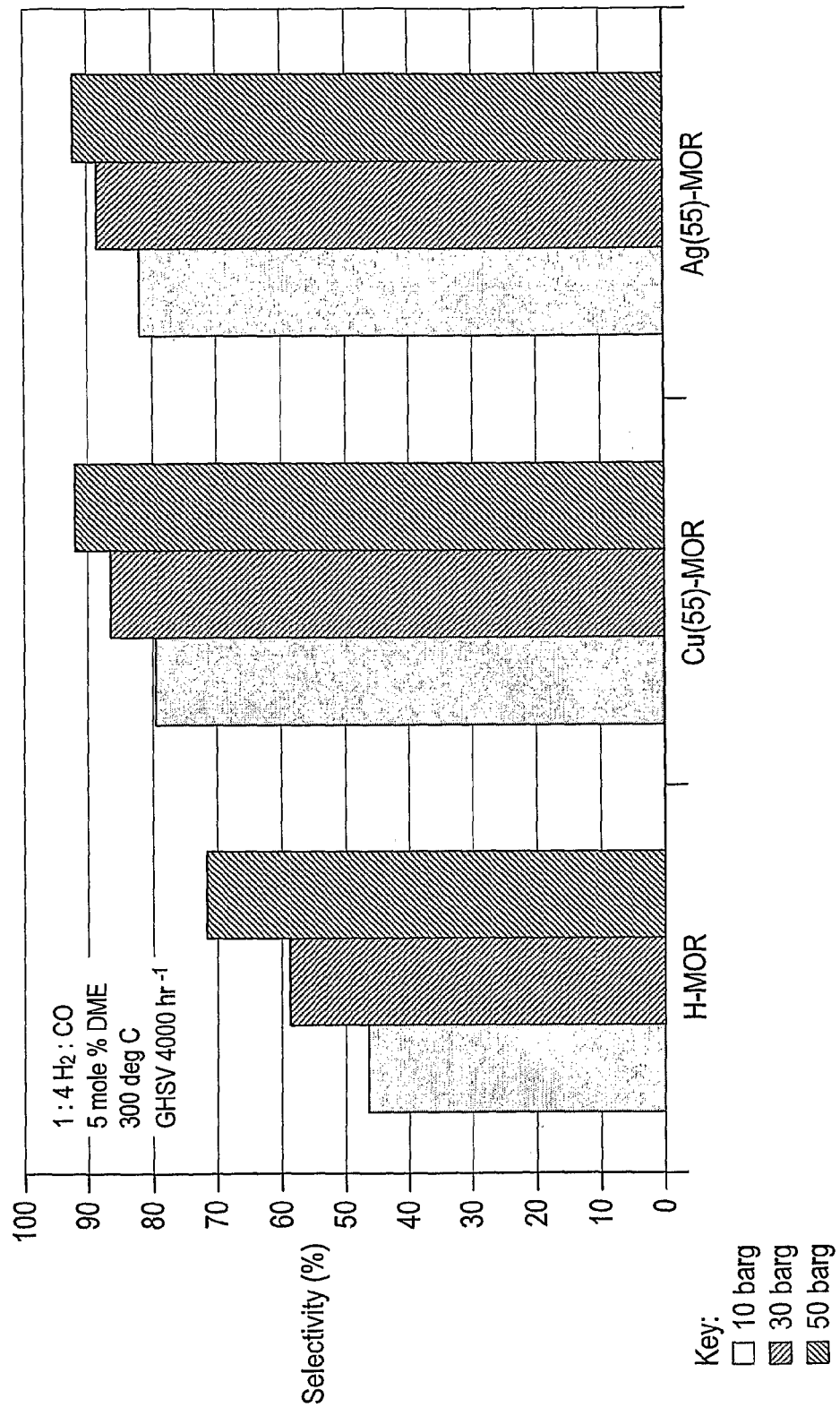

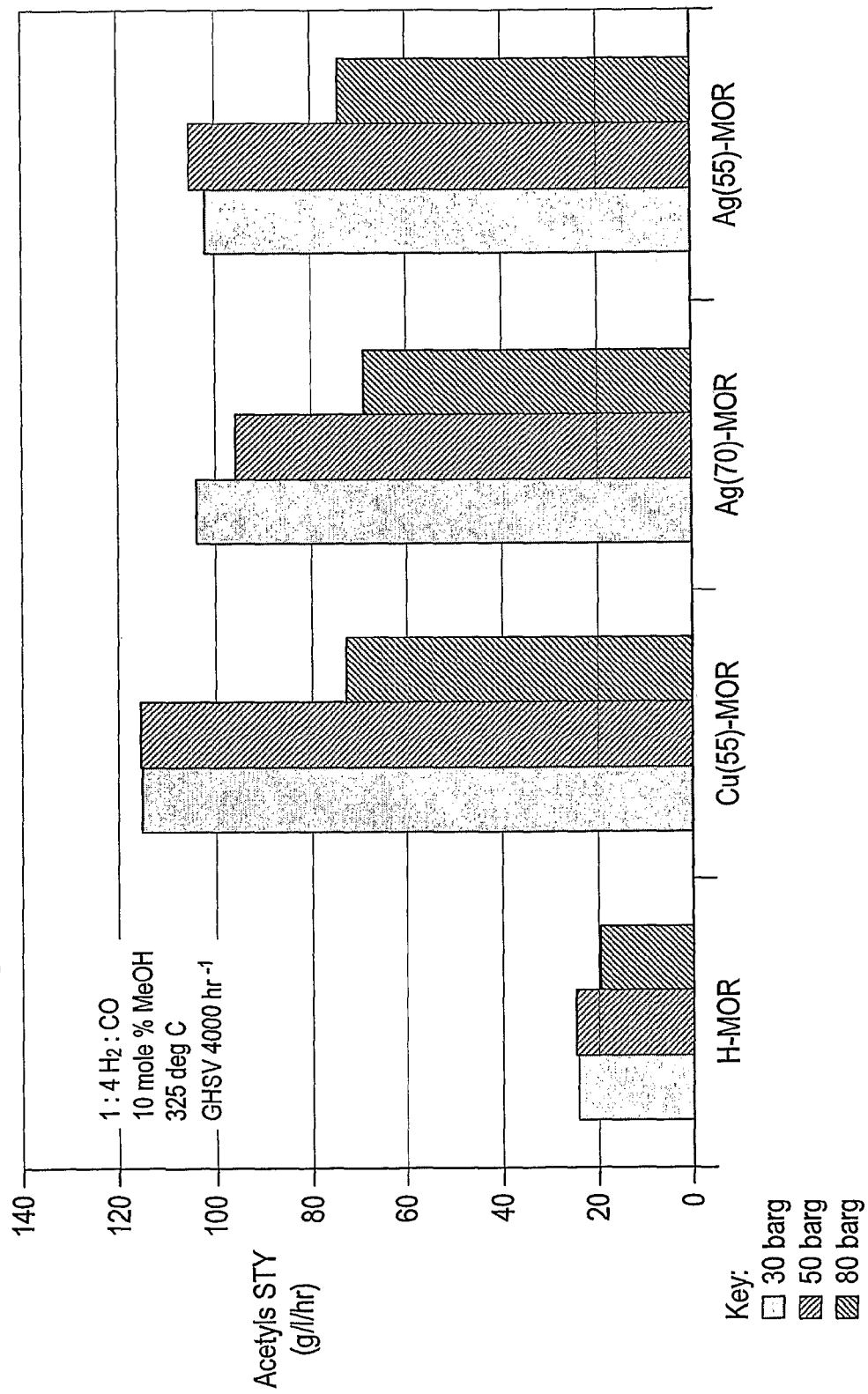

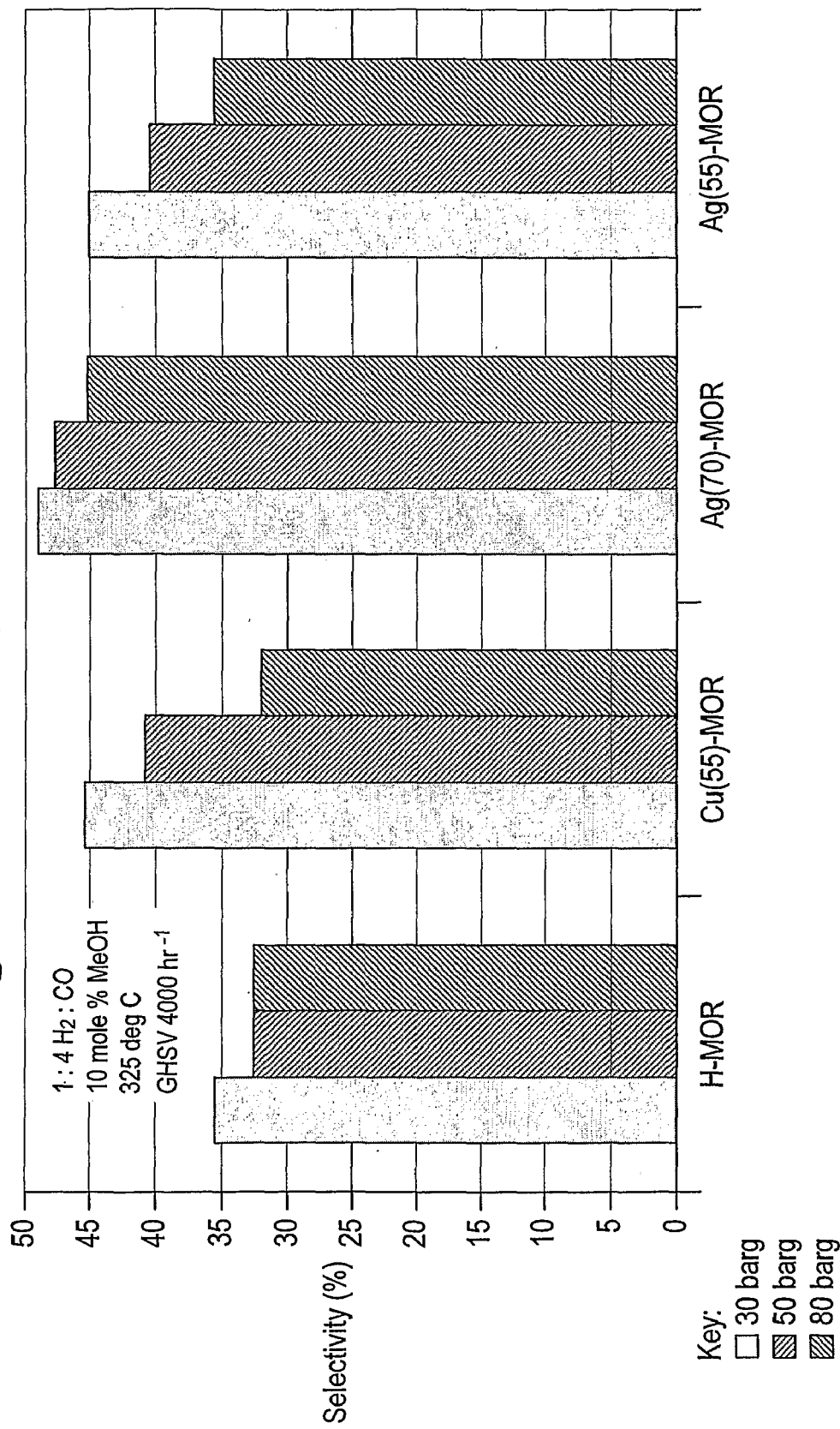

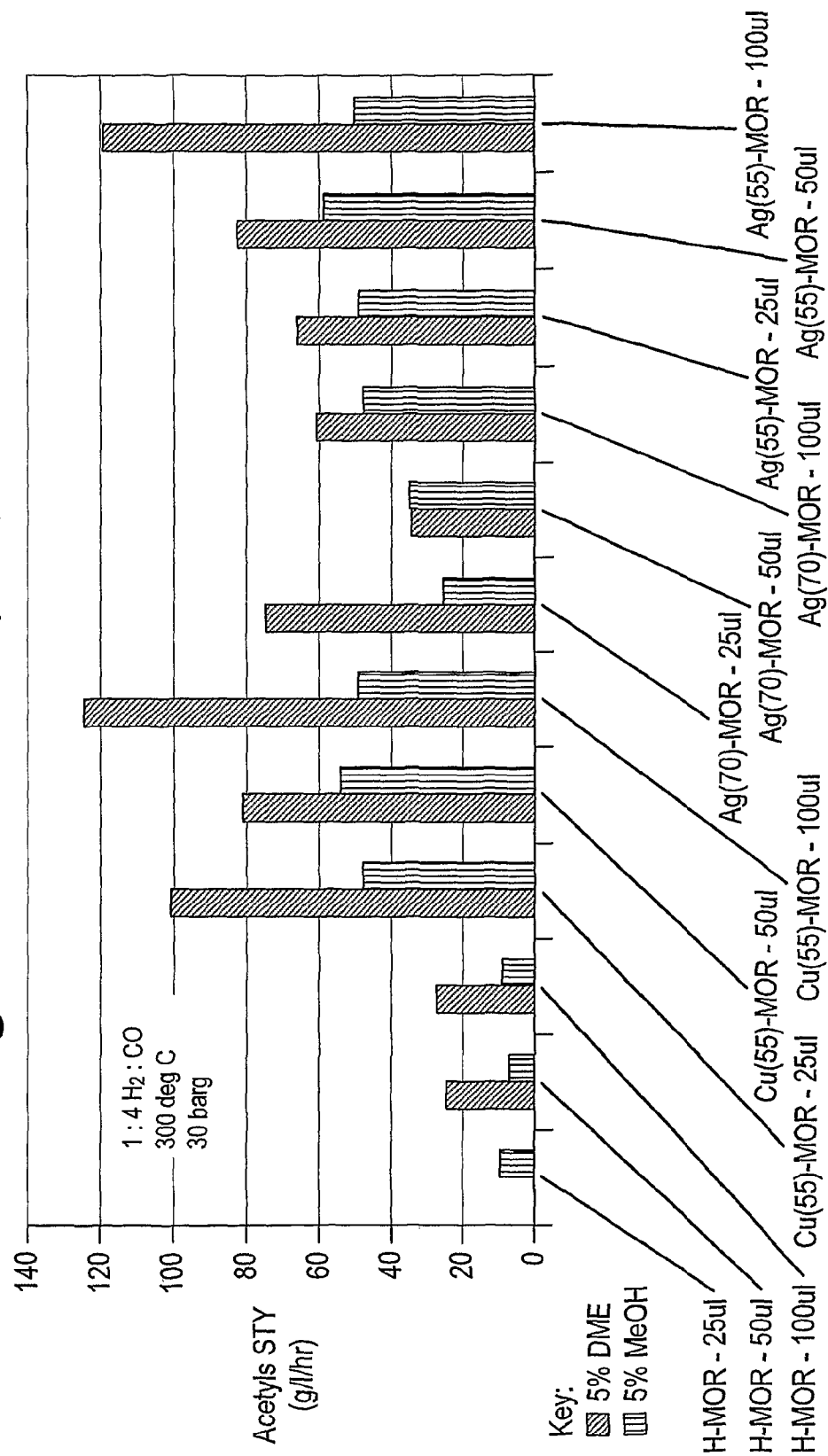
Fig. 9 DME vs MeOH comparison

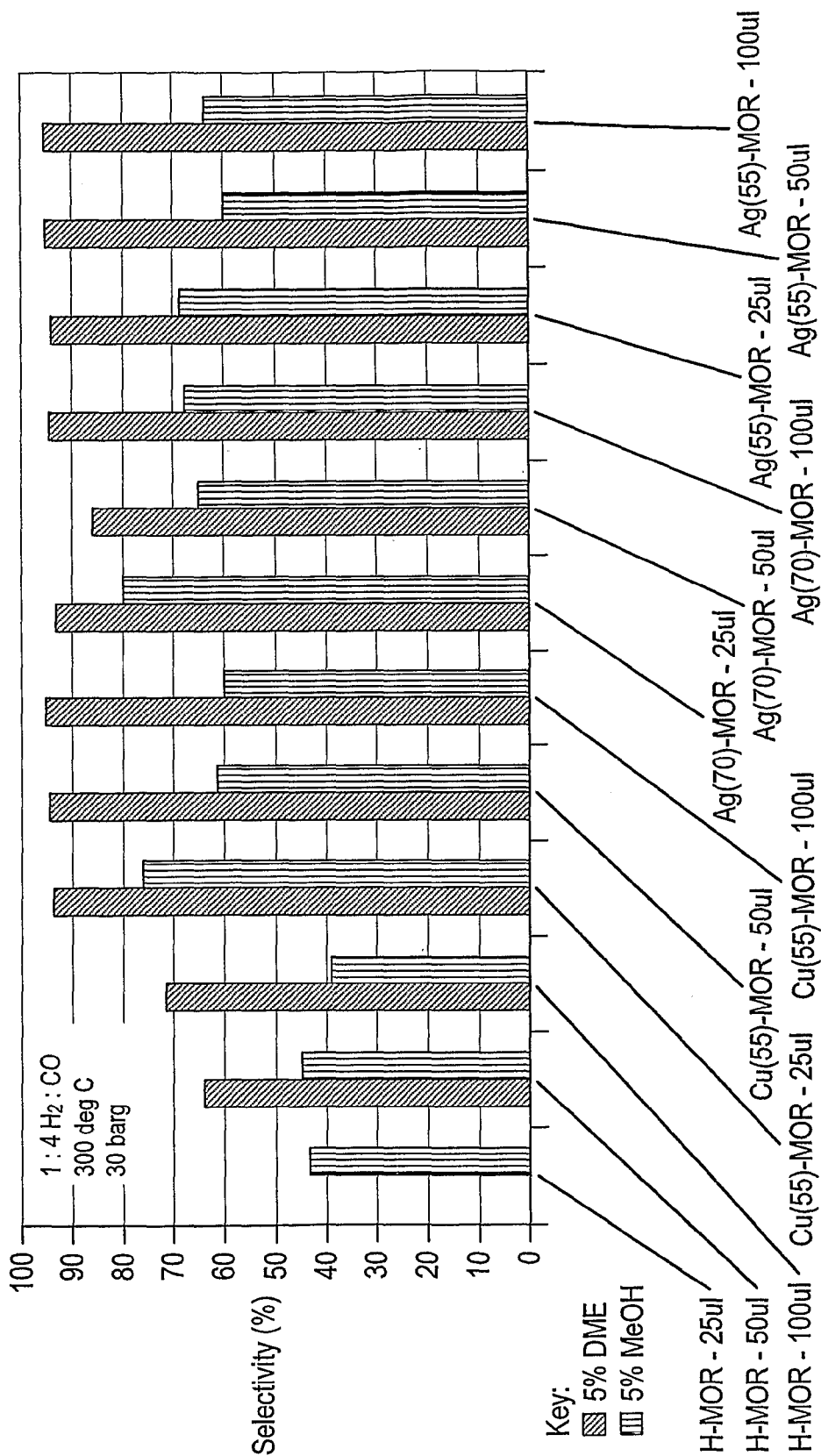

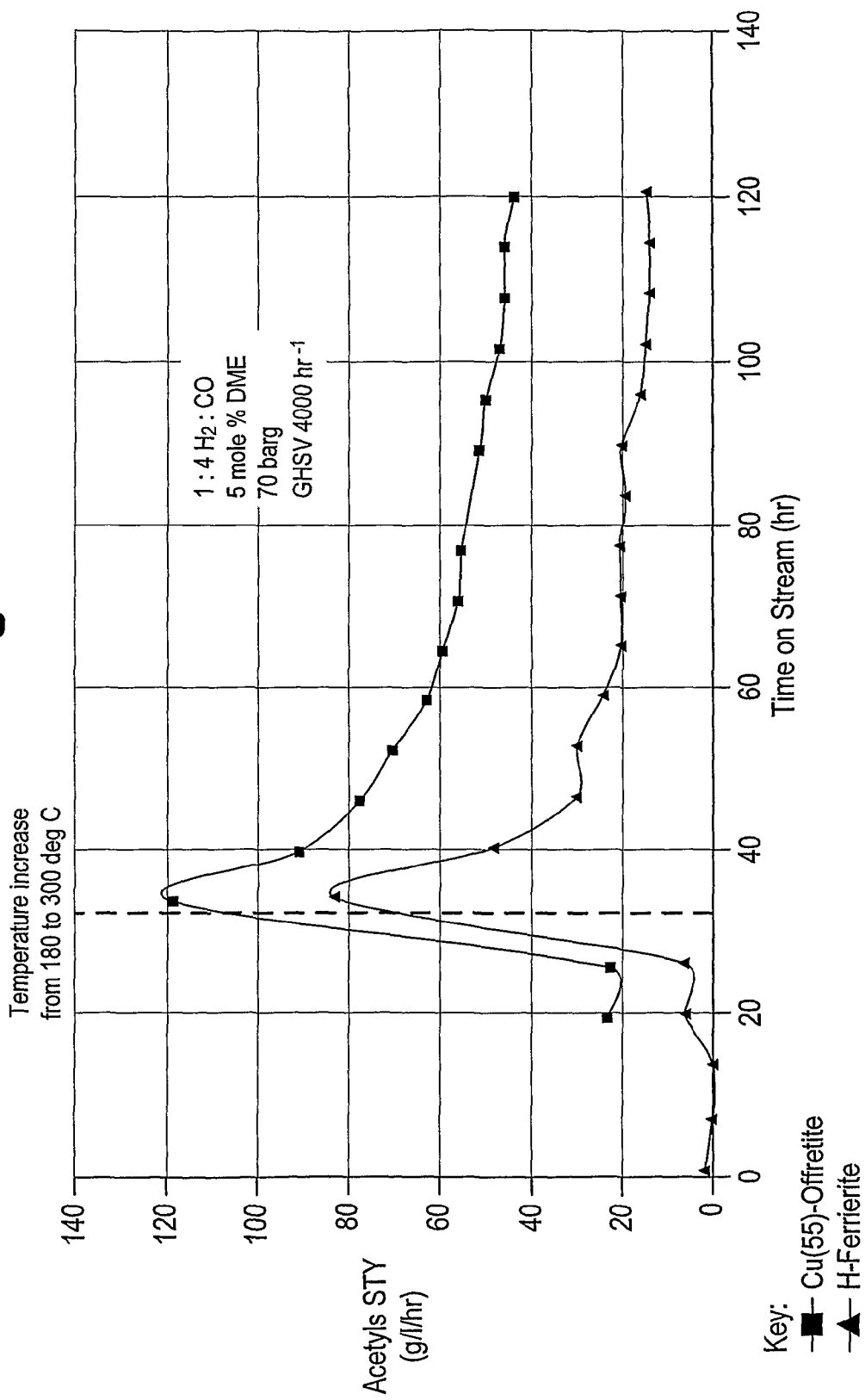

PROCESS FOR THE CARBONYLATION OF DIMETHYL ETHER

This application is the U.S. national phase of International Application No. PCT/GB2008/001474 filed 23 Apr. 2008, which designated the U.S. and claims priority to Europe Application No. 07251758.4 filed 26 Apr. 2007, the entire contents of each of which are hereby incorporated by reference.

This invention relates to a process for preparing methyl acetate by reacting dimethyl ether with carbon monoxide in the presence of a zeolite catalyst.

BACKGROUND OF THE INVENTION

Methyl acetate is used industrially in petrochemical processes, particularly as a feed for the production of acetic acid and/or acetic anhydride.

The commercial production of acetic acid is operated as a homogeneous liquid-phase process in which the carbonylation reaction is catalysed by a Group VIII noble metal such as rhodium or iridium and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous gas phase process using an iodide free solid catalyst could be developed.

EP-A-0 596 632 describes a vapour phase process for the carbonylation of methanol to produce acetic acid in the presence of a modified mordenite catalyst at high temperatures and pressures.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof. However, the use of zeolites to catalyse the carbonylation reaction is not exemplified.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of a modified mordenite catalyst at a temperature in the range 250-600° C. and a pressure in the range 10 to 200 bar. The use of dimethyl ether as a feedstock is not exemplified.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst. According to this patent application, the carbonylation process is run at temperatures at or below 250° C., and preferably from about 150 to about 180° C. to minimise by-product formation.

In view of the above-mentioned prior art, there remains the need for a heterogeneous gas phase process for the production of methyl acetate from dimethyl ether under substantially anhydrous conditions using a zeolite catalyst which is superior to the other processes using carbonylatable reactants as a feed.

SUMMARY OF THE INVENTION

It has now been found that if the carbonylation process is carried out at a temperature in the range of greater than 250° C. to 350° C. and at a pressure of greater than 10 barg then improved productivities and/or selectivities may be achieved.

Accordingly, the present invention provides a process for the production of methyl acetate which process comprises the carbonylation of a dimethyl ether feed with carbon monoxide under substantially anhydrous conditions, in the presence of a zeolite catalyst effective for said carbonylation, wherein said carbonylation is carried out at a temperature in the range of greater than 250° C. to 350° C. and at a pressure in the range greater than 10 barg to 100 barg.

The present invention solves the problem defined above by operating the process at high temperature and high pressure to give good selectivities and/or productivities to methyl acetate product. The finding that this can be achieved at high temperatures and pressures is surprising because from the work described in WO 2006/121778 mentioned above, it would be expected that the effect of increasing the reaction temperature of a zeolite-catalysed carbonylation of dimethyl ether would be merely to significantly reduce the methyl acetate formation rate and selectivity thereto. Furthermore, methanol carbonylation in the presence of a zeolite catalyst generally requires a reaction temperature of greater than 250° C. thus it would be expected that the productivities and/or selectivities achieved by the carbonylation of dimethyl ether under the same reaction conditions as the carbonylation of methanol would be inferior.

The dimethyl ether used as the feed in the process of the present invention may be substantially pure dimethyl ether. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. In the process of the present invention the dimethyl ether feed may comprise small amounts of methanol provided that the amount of methanol present in the feed is not so great as to inhibit the carbonylation of dimethyl ether to methyl acetate product. It has been found that less than 5 wt %, such as less than 1 wt % of methanol in the dimethyl ether feed may be tolerated.

Suitably, dimethyl ether is present in the feed at a concentration in the range of 0.1 to 20 mol %, for example 1 mol % to 20 mol %, such as 1.5 to 10 mol %, for example, 1.5 mol % to 5 mol %, based on the total feed (including recycles).

The carbon monoxide may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

The carbon monoxide feed may contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1, for example, 1:1 to 4:1.

The molar ratio of carbon monoxide to dimethyl ether is suitably in the range 1:1 to 99:1, such as 2:1 to 60:1.

The zeolite catalyst may be any zeolite which is effective to catalyse the carbonylation of dimethyl ether with carbon monoxide to produce methyl acetate.

Zeolites are available from commercial sources, generally in the Na, $NH_4$ form or H-form of the zeolite. The $NH_4$ form can be converted to the acid (H-form) by known techniques, such as calcination at high temperature. The Na form can be converted to the acid (H-form) by converting first to an $NH_4$ form by ion exchange with ammonium salts such as ammonium nitrate. Alternatively, zeolites may be synthesised using known techniques.

Zeolites comprise a system of channels which may be interconnected with other channel systems or cavities such as side-pockets or cages. The ring structures are generally 12-member rings, 10-member rings or 8 member rings. A zeolite may possess rings of different sizes. The zeolites for use in the present invention preferably contain at least one channel which is defined by an 8-member ring. Most preferably, the 8-member ring channel is interconnected with at least one channel defined by a ring with 10 and/or 12 members. The window size of the channel systems should be such that the reactant dimethyl ether and carbon monoxide molecules can diffuse freely in and out of the zeolite framework. Suitably, the window size of an 8-member ring channel may be at least 2.5×3.6 Angstroms. The *Atlas of Zeolite Framework Types* (C. Baerlocher, W. M. Meier, D. H. Olson, $5^{th}$ ed. Elsevier, Amsterdam, 2001) in conjunction with the web-based version (http://www.iza-structure.org/databases/) is a compendium of topological and structural details about zeolite frameworks, including the types of ring structures present in a zeolite and the dimensions of the channels defined by each ring type. Examples of zeolites suitable for use in the present invention include zeolites of framework type MOR, for example mordenite, FER, such as ferrierite, OFF, for example, offretite and GME, for example gmelinite.

For the process of the present invention it is preferred that the zeolite has a silica to alumina ratio of at least 5 but preferably less than or equal to 100, such as in the range 7 to 40, for example 10 to 30. Where the aluminium atoms have been replaced by framework modifier elements such as gallium, it is preferred that the ratio of silica:$X_2O_3$ where X is a trivalent element, such as aluminium, gallium, iron and/or boron, is at least 5 and preferably less than or equal to 100, such as in the range 7 to 40, for example 10 to 30.

In one embodiment of the present invention the zeolite catalyst is a mordenite, zeolite. The mordenite may be employed in the acid form (H-mordenite) or it may be optionally ion-exchanged or otherwise loaded with one or more metals such as copper, silver, nickel, iridium, rhodium, platinum, palladium or cobalt.

The metal loading on the mordenite zeolite may be expressed in terms of the fractional loading of the metal as gram atoms of metal per gram atom of aluminium in the mordenite. The metal loading can also be expressed as a mole percentage loading relative to aluminium in the mordenite through the relationship:

$$\text{mol \% Metal} = (\text{gram atoms Metal/gram atoms aluminium}) \times 100$$

Thus, for example, a loading of 0.55 gram atoms of copper per aluminium in the mordenite equates to a 55 mol % loading of copper relative to aluminium in the mordenite.

Suitably, the metal loading may be in the range of 1 to 200 mol % relative to aluminium, such as 50 to 120 mol %, for example, 50 to 110 mol % or 55 to 120 mol %, such as 55 to 110 mol %.

The mordenite framework, may in addition to the silicon and aluminium atoms, contain additional trivalent elements, such as boron, gallium and/or iron.

Where the mordenite contains at least one or more trivalent framework, the metal loading in the mordenite can be expressed in terms of the fractional loading of the metal as gram atoms of metal per gram atom of total trivalent elements in the mordenite. The metal loading can also be expressed as a mole percentage loading relative to total trivalent elements in the mordenite through the relationship:

$$\text{mol \% Metal} = (\text{gram atoms Metal/gram atoms of total trivalent elements}) \times 100$$

Because the carbonylation reaction is to be conducted substantially in the absence of water, it is preferred that the zeolite catalyst is dried prior to use. The zeolite may be dried, for example by heating to a temperature of 400 to 500° C.

It is preferred that the zeolite catalyst is activated immediately before use by heating the zeolite at elevated temperature for at least one hour under flowing nitrogen, carbon monoxide, hydrogen or mixtures thereof.

The process is carried out under substantially anhydrous conditions, i.e in the substantial absence of water. The carbonylation of dimethyl ether to methyl acetate does not generate water in-situ. Water has been found to inhibit the carbonylation of dimethyl ether to form methyl acetate. Thus, in the process of the present invention, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate. Suitably, less than 2.5 wt % water, for example, less than 0.5 wt % water may be present in the dimethyl ether feed.

The process of the present invention is carried out at a temperature in the range of greater than 250° C. to 350° C. and at a pressure in the range greater than 10 barg to 100 barg. Suitably, the temperature may be in the range 275 to 350° C., for example, 300 to 350° C. or 275 to 325° C.

Suitably, the pressure may be in the range greater than 10 barg to 80 barg, for example, greater than 10 barg to 50 barg, 15 to 80 barg, 15 to 50 barg, 30 barg to 80 barg and 30 barg to 100 barg, for example 50 barg to 100 barg.

Suitably, the process may be carried out at a temperature in the range 275 to 350° C., such as 300 to 350° C. and at a pressure of greater than 10 barg to 100 barg, for example, greater than 10 barg to 80 barg, such as 15 to 50 barg and 30 barg to 80 barg.

The Gas Hourly Space Velocity (GHSV) is suitably in the range 500 to 40,000 $h^{-1}$, for example, 1000 to 20,000 $h^{-1}$, such as 2000 to 20,000 $h^{-1}$.

The process of the present invention is suitably carried out by passing dimethyl ether vapour and carbon monoxide gas through a fixed or fluidised bed of the zeolite catalyst maintained at the required temperature and pressure.

Preferably, the process of the present invention is carried out substantially in the absence of halides, such as iodide. By the term 'substantially' is meant that the halide, for example, iodide content of the reactant gases (dimethyl ether and carbon monoxide) and catalyst is less than 500 ppm, preferably less than 100 ppm.

The primary product of the process is methyl acetate but small amounts of acetic acid may also be produced. The methyl acetate produced by the process of the present invention can be removed in the farm of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

The process may be operated as either a continuous or a batch process, preferably as a continuous process.

The invention is now illustrated with reference to the following Examples.

Catalyst Preparation

Catalyst A—H-Mordenite

H-Mordenite (H-MOR) with a silica to alumina ratio of 20 (ex Süd Chemie) was calcined in a muffle oven (oven-volume=18 L) under a static atmosphere of air. The temperature was increased from room temperature to 500° C. at a ramp rate of 5° C./min and then held at this temperature for 24 hours. The mordenite was then compacted at 12 tonnes in a 33 mm die set using a Specac Press, and then crushed and sieved to a particle size fraction of 212 to 335 microns.

Catalyst B—Cu-Mordenite-Cu(55)-MOR

H-Mordenite (40 g) with a silica to alumina ratio of 20 (ex Süd Chemie) was weighed into a 500 mL round bottomed flask together with 6.43 g of copper (II) nitrate hemipentahydrate (98% ACS) and a stirrer bar. Sufficient deionised water (ca. 100 mL) was then added to the flask until a thick slurry was obtained. The top of the flask was then loosely covered and the flask left to stir overnight. The zeolite was then dried under reduced vacuum using a rotary evaporator before being dried in an oven at 100° C. for 12 hours. The zeolite was then calcined in a muffle oven (oven volume=18 L) under a static atmosphere of air. The temperature was increased from room temperature to 500° C. at a ramp rate of 5° C./min and then held at this temperature for 24 hours. The zeolite was then compacted at 12 tonnes in a 33 mm die set using a Specac Press, and then crushed and sieved to a particle size fraction of 212 to 335 microns. The zeolite had a Cu loading of 55 mole % relative to Al contained in the mordenite.

Catalyst C—Ag-Mordenite-Ag(55)-MOR

This zeolite was prepared in the same way as for Preparation B except that silver nitrate (99+% ACS) (7.16 g for 50 g mordenite) was used instead of copper (II) nitrate hemipentahydrate (98% ACS). This resulted in a mordenite having a Ag loading of 55 mole % relative to Al contained in the mordenite.

Catalyst D—Ag-Mordenite-Ag(70)-MOR

This zeolite was prepared in the same way as for Preparation B except that silver nitrate (99+% ACS) (1.82 g for 10 g mordenite) was used instead of copper (II) nitrate hemipentahydrate (98% ACS). This resulted in a mordenite having a Ag loading of 70 mole % relative to Al contained in the mordenite.

EXAMPLE 1

Carbonylation of Dimethyl Ether

Dimethyl ether was carbonylated with carbon monoxide in the presence of zeolite catalysts A to C, at a range of temperatures 220-350° C. and at a range of pressures 10-50 barg. The experiments were carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Into each tube 50, 100 or 200 micro liters of a zeolite catalyst (designed to give GHSVs corresponding to 4000, 2000 and 1000 $h^{-1}$ respectively) is loaded onto a metal sinter having a pore size of 20 micrometers. All zeolite catalyst samples were heated at a ramp rate of 5° C./min. to 100° C. under 98.6 mole % $N_2$ and 1.4 mole % He at atmospheric pressure at a flow rate of 3.4 ml/min, and held at this temperature for 1 hour. The reactor was then pressurised to 10 barg and the system held at this condition for 1 hour. The gas feed was then changed to a mixture comprising 63.1 mole % carbon monoxide, 15.8 mole % hydrogen, 19.7 mole % nitrogen and 1.4 mole % He at a gas flow rate of 3.4 ml/min, and the system was heated at a ramp rate 3° C./min. to a temperature of 300° C. The system was then held at this condition for 3 hours. After this the temperatures of blocks 1 to 4 were adjusted to 220, 250, 300 and 350° C. respectively, and the system was allowed to stabilise for 10 minutes. At this point catalyst activation was considered complete, and the gas feed was changed to a mixture comprising 63.1 mole % carbon monoxide, 15.8 mole % hydrogen, 14.8 mole % nitrogen, 1.4 mole % He and 4.9 mole % dimethyl ether at a gas flow rate of 3.4 ml/min. The reaction was allowed to continue for ca. 78.6 hours under the above conditions and then the pressure was increased from 10 to 30 barg and the system was allowed to stabilise for 30 minutes. These conditions were maintained for ca. 28 hours, and then the pressure was increased from 30 barg to 50 barg. The system was again allowed to stabilise for 30 minutes and then held at these conditions for a further 28 hours. The exit stream from the reactor was passed to two gas chromatographs. One of these was a Varian 4900 micro GC with three columns (Molecular sieve 5A, Porapak® Q, and CP-Wax-52) each quipped with a thermal conductivity detector. The other was an Interscience Trace GC with two columns (CP-Sil 5 and CP-Wax 52) each equipped with a flame ionisation detector. Data was averaged between 50.1 and 78.6 hours to generate the 10 barg results; between 78.6 and 107.1 hours to generate the 30 barg results and between 107.1 and 135.6 hours to generate the 50 barg results.

The productivity and selectivity results of the dimethyl ether carbonylation reactions are shown in FIGS. 1 to 6. Productivity, $STY_{acetyls}$ is defined as the STY for the production of AcOH plus the STY for the production of MeOAc multiplied by $MW_{AcOH}/MW_{MeOAc}$. Selectivity was calculated on the basis of ([MeOAc]out+[AcOH]out)/([DME]in−[DME]out−0.5*[MeOH]out−0.5*[MeOAc]out)*100.

BRIEF DESCRIPTION OF THE DRAWINGS

The invention is further described with reference to the accompanying drawings, in which:

FIG. 1 depicts productivities achieved at a reaction pressure of 50 barg for each of the reaction temperatures 220, 250, 300 and 350° C.

FIG. 2 depicts selectivities to the carbonylation products, methyl acetate and acetic acid, achieved at a reaction pressure of 50 barg for each of the reaction temperatures 220, 250, 300 and 350° C.

FIG. 3 depicts productivities achieved at a reaction pressure of 30 barg for each of the reaction temperatures 220 250 300 and 350° C.

FIG. 4 depicts selectivities to the carbonylation products, methyl acetate and acetic acid, achieved at a reaction pressure of 30 barg for each of the reaction temperatures 220, 250. 300 and 350° C.

FIGS. 5 and 6 depict productivities and selectivities respectively achieved by operating at a pressure of 10 barg, 30 barg or 50 barg. and at a temperature of 300° C.

FIGS. 7 and 8 depict the productivity and selectivity results for carbonylation at 325° C. and at pressures of 10 barg, 30 barg and 50 barg.

FIGS. 9 and 10 depict the productivities and selectivities achieved using catalysts A to D.

FIG. 11 depicts the productivity results with respect to the carbonylation of dimethyl ether using catalysts E and F.

As can be seen from FIGS. 1-4, superior productivities and selectivities are achieved by operating an anhydrous dimethyl ether carbonylation process at temperatures of greater than 250° C. and at a pressure greater than 10 barg.

EXPERIMENT A

Carbonylation of Methanol

Methanol was carbonylated with carbon monoxide in the presence of zeolite catalysts A to D. The experiments were carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Into each tube 25, 50 or 100 micro liters of zeolite catalyst (designed to give GHSVs corresponding to 4000, 2000 and 1000 h$^{-1}$ respectively) is loaded onto a metal sinter having a pore size of 20 micrometers. All catalyst samples were heated at a ramp rate of 5° C./min. to 100° C. under 98.8 mole % $N_2$ and 1.2 mole % Heat atmospheric pressure at a flow rate of 3.4 ml/min, and held at this temperature for 1 hour. The reactor was then pressurised to the desired pressure (30 barg, 50 barg or 80 barg) and the system held at the desired pressure for 1 hour. The gas feed was then changed to a mixture comprising 63.2 mole % carbon monoxide, 15.8 mole % hydrogen, 19.8 mole % nitrogen, and 1.2 mole % He at a gas flow rate of 3.33 ml/min, and the system was heated at a ramp rate 3° C./min. to a temperature of 300° C. The system was then held at this condition for 3 hours. After this the temperatures of blocks 1 to 4 were adjusted to 275, 300, 325 and 350° C. respectively, and the system was allowed to stabilise for 10 minutes. At this point catalyst activation was considered complete, and the gas feed was changed to a mixture comprising 63.2 mole % carbon monoxide, 15.8 mole % hydrogen, 9.9 mole % nitrogen and 1.2 mole % He and 9.9 mol % methanol at a gas flow rate of 3.4 ml/min. Methanol was fed as a liquid to the inlet of each reactor where it evaporated to give the afore-mentioned gas feed composition. The reaction was allowed to continue for at least 56.5 hours under the above conditions The exit stream from the reactor was passed to two gas chromatographs. One of these was a Varian 4900 micro GC with three columns (Molecular sieve 5A, Porapak® Q, and CP-Wax-52) each quipped with a thermal conductivity detector. The other was an Interscience Trace GC with two columns (CP-Sil 5 and CP-Wax 52) each equipped with a flame ionisation detector. For each of the runs data was averaged over a 28.5 hour period between ca. 27.8 and 56.3 hours.

The productivity and selectivity results for carbonylation at 325° C. and at pressures of 10 barg, 30 barg and 50 barg are given in FIGS. 7 and 8. Productivity, $STY_{acetyls}$ is defined as the STY for the production of AcOH plus the STY for the production of MeOAc multiplied by $MW_{AcOH}/MW_{MeOAc}$. Selectivity was calculated as ([MeOAc]out+[AcOH]out)/ ([MeOH]in−[MeOH]out−(2*[Me2O]out)−[MeOAc]out) *100.

From FIGS. 7 and 8, it can be seen the productivities and selectivities for the methanol carbonylation reactions decrease with increasing pressure. This is in direct contrast with the productivities and selectivities for the dimethyl ether reactions shown in FIGS. 5 and 6 which increase with increasing pressure.

EXAMPLE 2

Carbonylation of Dimethyl Ether

Example 1 was repeated using 25, 50 and 100 microliters of Catalysts A to D in the reactors (designed to give GHSV's corresponding to 8000, 4000 and 2000 h$^{-1}$ respectively). The reactors were pressurised to 30 barg and the temperature of blocks 1 to 4 was adjusted to 275, 300, 325 and 350 C. The reaction was run with a feed gas composition of 63.1 mol % carbon monoxide, 15.8 mol % hydrogen, 14.8 mol % nitrogen, 1.4 mol % helium and 4.9 mol % dimethyl ether at a gas flow rate of 3.4 ml/min for 93 hours. Productivity and selectivity data was averaged over a 27 hour period from 65 to 93 hours. FIGS. 9 and 10 depict the productivities and selectivities achieved respectively.

EXPERIMENT B

Carbonylation of Methanol

Experiment A was repeated using a pressure of 30 barg and with a reaftion feed gas composition of 63.25 mol % carbon monoxide, 15.8 mol % hydrogen, 14.8 mol % nitrogen, 1.2 mol % helium and 4.95 mol % methanol at a gas flow rate of 3.4 mol/min. The reaction was allowed to run for 92 hours. Productivity and selectivity data was averaged over the period from 65.5 to 92.1 hours. FIGS. 9 and 10 depict the productivities and selectivities achieved respectively.

Methanol carbonylation in the presence of a zeolite catalyst generally requires a reaction temperature of greater than 250° C. to achieve acceptable reaction rates. It has been the view that the carbonylation of dimethyl ether in the presence of a zeolite catalyst requires the converse, i.e a reaction temperature below 250° C. However, FIGS. 9 and 10 clearly demonstrate that by operating a zeolite-catalysed carbonylation of dimethyl ether at both high pressure and high temperature, not only are high productivities and selectivities achieved but these productivities and selectivities are superior to those obtained in the carbonylation of methanol employing the same catalysts under the same reaction conditions.

EXAMPLE 3

Catalyst Preparation

Catalyst E—H-Ferrierite $NH_4$-Ferrierite with a silica to alumina ratio of 55 (ex Zeolyst) was calcined in a muffle oven under a static atmosphere of air. The temperature was increased from room temperature to 110° C. at a ramp rate of 5° C./min. and held at this temperature for 2 hours. The temperature was then increased to 450° C. at a ramp rate of 5° C./min and held at this temperature for 12 hours. The H-ferrierite was then compacted at 12 tonnes in a 33 mm die set using a Specac Press, and then crushed and sieved to a particle size fraction of 212 to 335 microns.

Catalyst F—Cu-Offretite-Cu(55)-Offretite

To 0.3 grams of $NH_4$-Offretite with a silica to alumina ratio of 10 (ex Sintef) was added 430 micro liters of a solution containing 0.3 grams of copper (II) nitrate hemipentahydrate (98% ACS) per ml of water. Additional water (to make the total amount of solution added up to ca. 700 micro liters) was added at the same time and the resultant slurry agitated on a roller bench for at least 1 hour to ensure thorough mixing. The zeolite was then dried at 50° C. for at least 16 hours, then at 110° C. for 4 hours before being calcined in a muffle furnace under a static atmosphere of air. The temperature for calcination was increased from room temperature to 500° C. at a rate of 2° C./min. and then held at this temperature for 2 hours. The Cu loaded offretite was then compacted at 12 tonnes in a 33 mm die set using a Specac Press, and then crushed and sieved to a particle size fraction of 212 to 335 microns. The Cu-offretite had a Cu loading of ca. 55 mole % relative to Al contained in the offretite.

Carbonylation of Dimethyl Ether

Example 1 was repeated using 50 micro liters of catalysts E and F in the reactors (designed to give a GHSV of 4000 hr$^{-1}$), at a pressure of 70 Barg. After holding the temperature of the reactors at 300° C. for 3 hours the temperature was adjusted to 180° C. and the system allowed to stabilise for 10 minutes before the gas feed was changed to a mixture comprising 63.1 mol % carbon monoxide, 15.8 mol % hydrogen, 14.8 mol % nitrogen, 1.4 mol % helium and 4.9 mol % dimethyl ether at a gas flow rate of 3.4 ml/min. The reaction was allowed to run under these conditions for 32.2 hours before the temperature was increased to 300° C. Reaction was then allowed to continue for a further 88 hours. The productivity results are depicted in FIG. 11.

The invention claimed is:

1. A process for the production of methyl acetate which process comprises the carbonylation of a dimethyl ether feed with carbon monoxide under substantially anhydrous conditions, in the presence of a zeolite catalyst effective for said carbonylation, wherein said carbonylation is carried out at a temperature in the range of 275 to 350° C. and at a pressure in the range of greater than 10 barg to 100 barg.

2. A process according to claim 1 wherein the temperature is in the range 300 to 350° C.

3. A process according to claim 1 wherein the pressure is in the range greater than 10 barg to 80 barg.

4. A process according to claim 3 wherein the pressure is in the range 15 to 80 barg.

5. A process according to claim 4 wherein the pressure is in the range 30 to 80 barg.

6. A process according to claim 1 wherein the carbonylation is carried out in the presence of hydrogen.

7. A process according to claim 1 wherein the zeolite contains at least one channel which is defined by an 8-member ring.

8. A process according to claim 7 wherein the zeolite is selected from the group consisting of mordenite, ferrierite, offretite and gmelinite.

9. A process according to claim 8 wherein the mordenite is H-mordenite or is ion-exchanged or otherwise loaded with at least one metal selected from the group consisting of copper, nickel, iridium, silver, rhodium, platinum, palladium and cobalt.

10. A process according to claim 9 wherein the mordenite is ion-exchanged or otherwise loaded with a metal selected from copper, silver and mixtures thereof.

11. A process according to claim 10 wherein the metal loading is in the range 50 to 120 mol % relative to aluminium.

12. A process according to claim 1 wherein at least some of the methyl acetate product is hydrolysed to acetic acid.

* * * * *